US00PP24706P2

(12) United States Plant Patent
van der Spek

(10) Patent No.: US PP24,706 P2
(45) Date of Patent: Jul. 29, 2014

(54) *HYDRANGEA* PLANT NAMED 'SANDY SUMMER'

(50) Latin Name: *Hydrangea macrophylla×serrata*
Varietal Denomination: Sandy Summer

(75) Inventor: Daan van der Spek, Nootdorp (NL)

(73) Assignee: Flower Time II, Center Moriches, NY (US)

( * ) Notice: Subject to any disclaimer, the term of this patent is extended or adjusted under 35 U.S.C. 154(b) by 174 days.

(21) Appl. No.: 13/506,045

(22) Filed: Mar. 22, 2012

(51) Int. Cl.
*A01H 5/00* (2006.01)

(52) U.S. Cl.
USPC ..... Plt./250

(58) Field of Classification Search
CPC ..... A01H 5/02
USPC ..... Plt./250
See application file for complete search history.

(56) References Cited

U.S. PATENT DOCUMENTS

PP20,124 P2 * 6/2009 van der Spek ..... Plt./250
PP20,125 P2 * 6/2009 Gossett ..... Plt./479
PP20,145 P2 * 6/2009 van der Spek ..... Plt./250

OTHER PUBLICATIONS

Niemiera. Bigleaf *Hydrangea Hydrangea macrophylla*. Virginia Cooperative Extension Service, 3010-1463, 2010, pp. 1-2.*

* cited by examiner

*Primary Examiner* — June Hwu
(74) *Attorney, Agent, or Firm* — Cassandra Bright

(57) ABSTRACT

A new and distinct *Hydrangea* cultivar named 'Sandy Summer' is disclosed, characterized by a full, round mophead type inflorescence and pink petal with thin white margin coloration and unique serrate petal margins. Plants are characteristically strong and resistant to breaking, and produce dark green foliage. The new variety is a Hydrangea, normally used for ornamental indoor or outdoor purposes.

1 Drawing Sheet

Latin name of the genus and species: *Hydrangea macrophylla×serrata.*

Variety denomination: 'Sandy Summer'.

BACKGROUND OF THE INVENTION

The new cultivar is a product of a planned breeding program. The intent of the breeder program was to develop *Hydrangea* varieties with strong stems and attractive flower colors. The new variety was discovered as seedling within the planned breeding program. This seedling is a result from the crossing of the female parent, an undistributed proprietary variety referred to as 9626 with the male parent, an undistributed proprietary variety referred to as 9658. It was selected by Daniel van der Spek in May of 2002 in Nootdorp, the Netherlands.

Asexual reproduction of the new cultivar 'Sandy Summer' by vegetative cuttings was first performed in Nootdorp, the Netherlands during 2002 and has shown that the unique features of this cultivar are stable and reproduced true to type on successive generations.

Asexual reproduction of the new cultivar 'Sandy Summer' by vegetative cuttings was performed in Nootdorp, the Netherlands and has shown that the unique features of this cultivar are stable and reproduced true to type through 6 successive generations.

SUMMARY OF THE INVENTION

The cultivar 'Sandy Summer' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Sandy Summer' These characteristics in combination distinguish 'Sandy Summer' as a new and distinct *Hydrangea* cultivar:

1. Full, round mophead inflorescence.
2. Unique sepal coloration, pink sepal with a thin creamy white margin.
3. Dark green foliage.
4. Strong plant, resisting breaking in production and post-harvest situations.
5. Unique serration to sepal margins.

PARENTAL COMPARISON

Plants of the new cultivar 'Sandy Summer' are similar to plants of the female parent, '9626' in most horticultural characteristics, however, plants of the new cultivar 'Sandy Summer' differ from '9626' in the following characteristics;

1. Flower color of 'Sandy Summer' is pink with a creamy white margin whereas '9626' is solid light pink.
2. 'Sandy Summer' has more flowers per inflorescence.
3. 'Sandy Summer' has a wider inflorescence.
4. 'Sandy Summer' is a shorter plant than '9626'.

Plants of the new cultivar 'Sandy Summer' are similar to plants of the male parent, '9658' in most horticultural characteristics, however, plants of the new cultivar 'Sandy Summer' differ from '9658' in the following characteristics;

1. 'Sandy Summer' is a shorter plant.
2. Flowers of 'Sandy Summer' have a creamy white margin whereas '9658' has solid color flowers.

COMMERCIAL COMPARISON

Plants of the new cultivar 'Sandy Summer' are similar to plants of the commercial variety 'Sidasand', U.S. Plant Pat. No. 20,145 in most horticultural characteristics. However, plants of the new cultivar 'Sandy Summer' differ from 'Sidasand' in producing an inflorescence that is a round, mophead, compared to the flattened lacecap of 'Sidasand'. Additionally, 'Sandy Summer' produces flowers colored pink on the interior, with a thin creamy white margin, whereas 'Sidasand' flowers are creamy white with a thin red-purple margin.

Plants of the new cultivar 'Sandy Summer' are similar to plants of the commercial variety 'Sidasora', U.S. Plant Pat. No. 20,148 in most horticultural characteristics. However, plants of the new cultivar 'Sandy Summer' differ from 'Sidasora' in producing sepals that are pink, with a thin white margin, whereas 'Sidasora' sepals are white at the base, and pink over the rest of the surface. Additionally, 'Sandy Summer' produces flowers with a distinctive serrated margin to the sepal not found in 'Sidasora'.

BRIEF DESCRIPTION OF THE PHOTOGRAPH

The accompanying photograph in FIG. 1 illustrates in full color a typical flower of 'Sandy Summer'. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Mini Chart, 2005 except where general terms of ordinary dictionary significance are used. The following observations and measurements describe 'Sandy Summer' plants grown in a poly house in Mattituck, N.Y., USA from approximately Spring 2010 to Summer 2011. The growing temperature ranged from 4.5° C. to 10° C. at night to 17° C. to 21° C. during the day. Plants have not been allow to freeze. Measurements and numerical values represent averages of typical flowering types.

Botanical classification: *Hydrangea macrophylla×serrata* 'Sandy Summer'.

PROPAGATION

Time to rooting: 19 to 21 days at approximately 20° C.
Root description: Fine, fibrous.

PLANT

Growth habit: Flowering perennial shrub.
Height: Approximately 32 cm.
Plant spread: Approximately 28 cm.
Growth rate: Moderate.
Branching characteristics: Branches easily from base.
Basal branching: Yes.
Length of lateral branches: Approximately 22 cm.
Number of lateral branches: Varies, depending on pinches given to plant. Normally 5 to 6 from 1 or 2 pinches.
Diameter of lateral branches: Approximately 0.6 cm.
Internode length: 4-6 cm.
Lateral branch shape: Round.
Lateral branch strength: Very strong.
Stem color, immature: Near RHS Yellow-Green 145A.
Stem color, mature: Near RHS Green 137C.
Stem pubescence: No.
Other stem or plant characteristics: Stems covered with lenticels at a density of approximately 12 lenticels per cm of stem.
- *Lenticel length.*—Approximately 0.1 cm.
- *Lenticel width.*—Approximately 0.005 cm.
- *Lenticel color.*—Near RHS Greyed-Purple N186C.

Number of leaves per lateral branch: Average 6.
Age of plant described: Approximately 1.5 year.

FOLIAGE

Leaf:
- *Arrangement.*—Opposite.
- *Compound or single.*—Single.
- *Average length.*—Approximately 10-12 cm.
- *Average width.*—Approximately 6-8 cm.
- *Shape of blade.*—Elliptic.
- *Apex.*—Acute
- *Base.*—Acute
- *Attachment.*—Stalked.
- *Margin.*—Serrate.
- *Texture of top surface.*—Glabrous.
- *Texture of bottom surface.*—Glabrous.
- *Leaf internode length.*—Approximately 4.5 cm.
- *Color.*—Young foliage upper side: Near R.H.S. Yellow-Green 144A. Young foliage under side: Near R.H.S. Yellow-Green 144B. Mature foliage upper side: Near R.H.S. Green 137A. Mature foliage under side: Near R.H.S. Green 137B.

Venation:
- *Type.*—Pinnate
- *Venation color upper side.*—Near R.H.S. Yellow-Green 144C.
- *Venation color under side.*—Near R.H.S. Yellow-Green 144D.
- *Durability of foliage to stresses.*—High.

Petiole:
- *Average length.*—Typically 1.5-3.0 cm.
- *Diameter.*—Approximately 0.3 cm.
- *Color.*—Near R.H.S. Yellow-Green 145A.
- *Texture, upper side.*—Glabrous.
- *Texture, under side.*—Glabrous.

FLOWER

Bloom period:
- *Blooming period.*—Naturally blooming July through August.
- *Blooming in greenhouse production.*—Approximately 90 days from dormant state to blooming.

Inflorescence:
- *Arrangement.*—Terminal corymb.
- *Commercial type.*—Mophead.
- *Panicle height.*—7-12 cm.
- *Panicle diameter.*—10-18 cm.
- *Quantity of flowers per inflorescence.*—Fertile flowers, approximately 25. Sterile Flowers, approximately 50-70.

Bud:
- *Bud shape fertile flowers*.—Globose with 5 connate petals.
- *Bud length fertile flowers*.—Approximately 5 mm.
- *Bud diameter fertile flowers*.—Approximately 5 mm.
- *Bud color fertile flowers*.—Near R.H.S. Red-Purple 67A.

Flower:
- *Shape*.—Globose.
- *Facing direction*.—Outward.
- *Diameter of entire flower*.—Fertile: Approximately 0.5 cm. Sterile: 3.5-5 cm.
- *Depth of flower*.—Fertile: Approximately 0.5 cm. Sterile: 0.5-1.5 cm.
- *Rate of opening*.—Individual flowers: Fully open approximately 4 days from the bud stage.
- *Flower longevity on plant*.—Fertile flowers: Approximately 4 weeks.
- *Sterile flowers*.—Approximately 4 weeks. Persistent or self-cleaning.: Persistent.
- *Fragrance*.—No.

Sepals, sterile:
- *Length of sepal*.—2.5 cm.
- *Width of sepal*.—2 cm.
- *Apex*.—Acute.
- *Shape of sepal*.—Connate.
- *Sepal margin*.—Serrate.
- *Sepal arrangement*.—Rotate.
- *Sepal number*.—Average 4.
- *Sepals fused*.—Yes.
- *Sepal appearance*.—Matte.
- *Sepal texture*.—Glabrous top and bottom.

Color:
- *Upper surface at first opening*.—Near RHS Red-Purple 67A with margin White N155C.
- *Upper surface at maturity*.—Near RHS Red-Purple 67C with margin White N155C.
- *Upper surface at fading*.—RHS Red-Purple 67D with margin White N155C.
- *Under surface at first opening*.—Near RHS Red-Purple 67A with margin White N155C.
- *Under surface at maturity*.—Near RHS Red-Purple 67C with margin White N155C.
- *Under surface at fading*.—Near RHS Red-Purple 67D with margin White N155C.

Petaloids: No.
Fragrance: None.

FERTILE FLOWERS

Number: 5.
Sepal texture: Glabrous
Sepal arrangement: Rotate.
Sepal length: 3 mm.
Sepal width: 2 mm.
Sepal shape: Elliptic
Sepal base shape: Acute.
Sepal apex shape: Acute.
Sepal margin: Entire.
Sepal color:
- *Upper side*.—Near RHS Yellow-Green 150B.
- *Under side*.—Near R.H.S. Yellow 2D.

Petal length: 0.5 cm.
Petal width: 2 cm.
Petal apex shape: Acute.
Petal shape: Connate.
Petal number: Average 5.
Petal fused: Yes.
Petal appearance: Matte.
Petal texture: Glabrous top and bottom.

PEDUNCLE

Length: Range from 2 to 6 cm.
Diameter: Approximately 0.3 cm.
Angle: Approximately 15 degrees (0 degrees=straight upright).
Strength: Strong.
Color: Near R.H.S. Green 143C.
Texture: Smooth.

PEDICEL

Length:
- *Fertile flower*.—0.75 cm.
- *Sterile*.—2.5 cm.

Diameter:
- *Fertile flower*.—1 mm.
- *Sterile*.—1.5 mm.

Angle:
- *Fertile flower*.—Approximately 25 degrees.
- *Sterile*.—45 to 75 degrees.

Strength: All pedicels sturdy.
Color:
- *Fertile flower*.—Near RHS Red-Purple 65D.
- *Sterile*.—Near RHS Red-Purple 67D.

Texture:
- *Fertile flower*.—Pubescent.
- *Sterile*.—Pubescent.

REPRODUCTIVE ORGANS

Fertile flowers only:
- *Number of pistil per flower*.—3.
- *Pistil length*.—1 mm.
- *Stigma shape*.—Forked
- *Stigma color*.—Near RHS Red-Purple 67D.
- *Style color*.—Near RHS 155B. Style length: less than 1 mm. Ovary Color: Near RHS 155B.
- *Stamens*.—12.
- *Anther shape*.—Kidney shaped and basally attached.
- *Anther size*.—1 mm.
- *Anther color*.—Near RHS Yellow 2C.
- *Pollen color*.—Near RHS Yellow 6A.
- *Pollen quantity*.—Scant.

Sterile flowers only:
- *Number of pistil per flower*.—1.
- *Pistil*.—Less than 1 mm.
- *Stigma color*.—Near RHS 1558.
- *Style color*.—Near RHS Green-Yellow 1C.
- *Style length*.—Less than 1 mm.
- *Ovary color*.—Near RHS Yellow-Green 150B.
- *Stamens*.—12.
- *Anther shape*.—Kidney shaped and basally attached.
- *Anther size*.—Less than 1 mm.
- *Anther color*.—Near RHS Green-Yellow 1C.

*Pollen color*.—Not observed.

OTHER CHARACTERISTICS

Disease and pest resistance: Neither resistance nor susceptibility to normal diseases or pests of *Hydrangea* has been observed in this variety.

Drought tolerance and cold tolerance: Semi-hardy perennial, tolerant of some high temperatures. Upper limit of temperature tolerance has not been observed, however, known to tolerate temperatures of at least up to 40° C. Lower limits have also not been observed, however, observed hardy to −15° C. No drought tolerance has been observed.

Fruit/seed production: No fruits/seeds detected to date.

What is claimed is:

1. A new and distinct cultivar of *Hydrangea* plant named 'Sandy Summer' as herein illustrated and described.

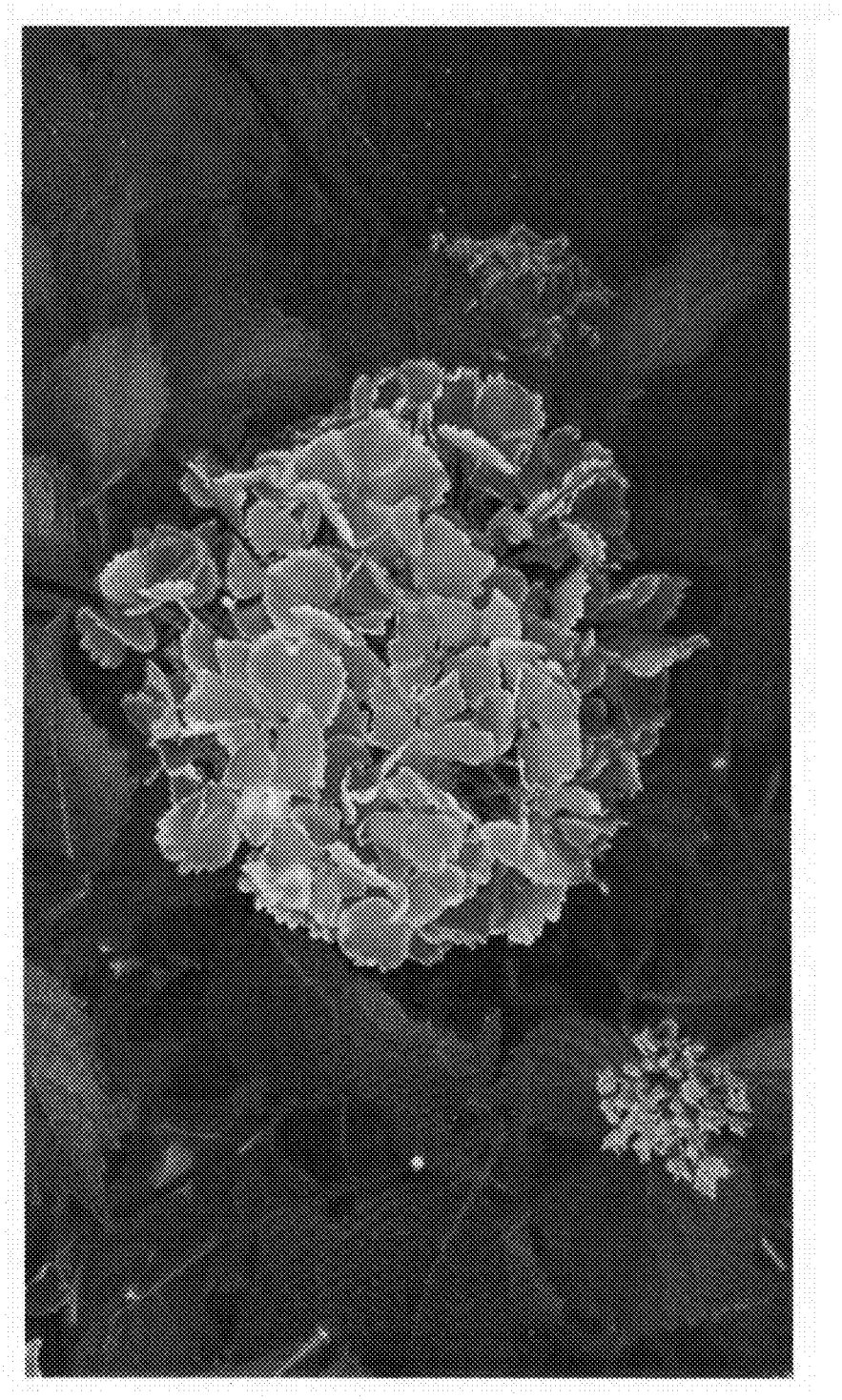

* * * * *